(12) United States Patent
Leinen et al.

(10) Patent No.: US 6,491,899 B1
(45) Date of Patent: Dec. 10, 2002

(54) ANTI-INFLAMMATORY DENTAL CARE AGENTS

(75) Inventors: Hans-Theo Leinen, Duesseldorf (DE); Peter Wuelknitz, Leichlingen (DE); Claudia Jassoy, Duesseldorf (DE)

(73) Assignee: Henkel Kommanditgesellschaft auf Aktien, Duesseldorf (DE)

( * ) Notice: Subject to any disclaimer, the term of this patent is extended or adjusted under 35 U.S.C. 154(b) by 0 days.

(21) Appl. No.: 09/744,822

(22) PCT Filed: Jul. 21, 1999

(86) PCT No.: PCT/EP99/05210
§ 371 (c)(1),
(2), (4) Date: Apr. 6, 2001

(87) PCT Pub. No.: WO00/06109
PCT Pub. Date: Feb. 10, 2000

(30) Foreign Application Priority Data

Jul. 30, 1998 (DE) .......................... 198 34 355

(51) Int. Cl.⁷ ................................................ A61K 7/16
(52) U.S. Cl. ........................................................ 424/49
(58) Field of Search ...................... 424/49–58

(56) References Cited

U.S. PATENT DOCUMENTS

| | | | |
|---|---|---|---|
| 3,538,230 A | | 11/1970 | Pader et al. ................... 424/50 |
| 3,992,519 A | * | 11/1976 | Hofmann et al. .............. 424/49 |
| 4,022,880 A | * | 5/1977 | Vinson et al. ................. 424/49 |
| 4,153,680 A | | 5/1979 | Seybert ......................... 424/49 |
| 4,332,791 A | * | 6/1982 | Raaf et al. ..................... 424/52 |
| 4,339,429 A | * | 7/1982 | Raaf et al. ..................... 424/49 |
| 4,795,628 A | * | 1/1989 | Afseth .......................... 424/54 |
| 4,824,661 A | * | 4/1989 | Wagner ......................... 424/52 |
| 4,985,235 A | * | 1/1991 | Kligman ....................... 424/49 |
| 5,100,653 A | * | 3/1992 | Campo .......................... 424/54 |
| 5,185,377 A | * | 2/1993 | Schewe et al. ............. 514/721 |
| 5,188,817 A | | 2/1993 | Ozick ........................... 424/49 |
| 5,236,699 A | * | 8/1993 | Libin ............................ 424/54 |
| 5,240,696 A | * | 8/1993 | Van Der Ouderaa et al. . 424/49 |
| 5,855,872 A | * | 1/1999 | Libin ............................ 424/49 |
| 5,945,089 A | * | 8/1999 | Libin ............................ 424/54 |

FOREIGN PATENT DOCUMENTS

| | | | |
|---|---|---|---|
| DE | 1030519 | * | 5/1958 |
| DE | 25 22 486 | | 11/1975 |
| DE | 2429033 | * | 1/1976 |
| DE | 2530241 | * | 2/1977 |
| DE | 31 14 493 | | 10/1982 |
| EP | 0353675 | | 2/1990 |
| EP | 0528468 | | 2/1993 |
| GB | 1514469 | | 6/1978 |
| HU | 205 000 (57 046) | | 3/1992 |
| JP | 08 133969 | | 5/1996 |

OTHER PUBLICATIONS

Haug 57046 Oral Vitamin Chemical Abstracts, vol. 116, No. 18, 1992, Abstract No. 181171 XP002124960 Derwent Acc –No. 1996–306469 Week 199631, 1996, Derwent Publications Ltd. London, GB (Lion Corp) JPX 08133969.

* cited by examiner

*Primary Examiner*—Shep K. Rose
(74) *Attorney, Agent, or Firm*—Stephen D. Harper

(57) ABSTRACT

The present invention relates to a dental care composition containing (a) at least one panthenol compound, (b) at least one retinol compound, and (c) at least one antibacterial compound. The composition is particularly useful for reducing inflammation of the gums.

16 Claims, No Drawings

ANTI-INFLAMMATORY DENTAL CARE AGENTS

FIELD OF THE INVENTION

This invention relates to dental care and cleaning preparations which counteract inflammation of the gums (gingivitis) through a special combination of active ingredients.

BACKGROUND OF THE INVENTION

Dental care preparations are primarily intended to remove food residues, discoloration and firmly adhering bacterial films from the surface of the teeth. In addition, attempts have been made to counteract diseases of the teeth and gums such as, for example, caries, gingivitis and parodontosis by incorporating special additives, for example fluorine compounds or antimicrobial agents, in dental care preparations.

A particularly stubborn disease which, unless successfully treated, can lead to the loosening and loss of teeth is periodontitis which, in its initial stages, is manifested in inflammation and bleeding of the gums (gingivitis). It is caused by bacteria which colonise the dental pockets and which are difficult to control by mechanical cleaning of the teeth with a toothbrush.

Attempts have been made to counteract inflammation of the gums by addition of antibacterial agents to toothpastes and mouthwashes. In most cases, however, conclusive results cannot be obtained in this way. Although certain non-cationic bactericidal agents, particularly from the group of chlorinated diphenylethers, have proved to be particularly effective, these compounds are not able on their own effectively to combat persistent inflammation of the gums.

A process for treating the periodontal tissue with a pharmaceutical composition containing a vitamin A derivative is known from U.S. Pat. No. 5,188,817. Toothpastes containing vitamin A have also been commercially available for some time (Aronal®).

It has now been found that the anti-inflammatory properties of, in particular, toothpastes already containing an antibacterial component can be significantly improved by addition of a combination of a panthenol or pantothenate and a retinol or retinol derivative.

SUMMARY OF THE INVENTION

Accordingly, the present invention relates to a dental care preparation with anti-inflammatory properties containing polishing components, fluorine compounds, humectants, binders, a water-insoluble non-cationic bactericidal component and water, characterized in that it contains a combination of panthenol or a salt of pantothenic acid and retinol or a retinol derivative to improve it anti-inflammatory properties.

DETAILED DESCRIPTION OF THE INVENTION

Dental care preparations in the context of the present invention are tooth powders, toothpastes, liquid tooth creams and tooth gels. Tooth. pastes and liquid tooth cleaning preparations are particularly suitable.

Suitable polishing components are, in principle, any of the known toothpaste abrasives, more particularly those which do not contain any calcium ions. Accordingly, particularly suitable polishing components are silicas, aluminium hydroxide, aluminium oxide, sodium aluminium silicates, organic polymers and mixtures of these abrasives.

However, calcium-containing polishing components such as, for example, chalk, calcium pyrophosphate or dicalcium phosphate dihydrate may be present in quantities of up to 5% by weight.

The total content of polishing components is preferably in the range from 5 to 50% by weight, based on the dental care preparation.

Toothpastes and liquid dental cleaning preparations which contain silicas as polishing component are particularly preferred. Suitable silicas are, for example, silica gels, silica hydrogels and precipitated silicas. Silica gels are obtained by reacting sodium silicate solutions with strong aqueous mineral acids to form a hydrosol, ageing to form the hydrogel, washing and drying. If drying is carried out under moderate conditions to a water content of 15 to 35% by weight, the so-called silica hydrogels known, for example, from U.S. Pat. No. 4,153,680 are obtained. Drying to water contents below 15% by weight results in irreversible shrinkage of the previously loose structure of the hydrogel to the dense structural of the so-called xerogel. Silica xerogels are described, for example, in U.S. Pat. No. 3,538,230.

A second particularly suitable group of silica polishing agents are the precipitated silicas. Precipitated silicas are obtained by precipitation of silica from dilute alkali metal silicate solutions by addition of strong acids under conditions which preclude aggregation to the sol and gel. Suitable processes for the production of precipitated silicas are described, for example, in DE-OS 25 22 486 and in DE-OS 31 14 493. A particularly suitable precipitated silica is that produced in accordance with DE-OS 31 14 493 which has a BET surface of 15 to 110 $m^2/g$, a particle size of 0.5 to 20 $\mu m$ (at least 80% by weight of the primary particles should be below 5 $\mu m$ in size) and a viscosity in the form of a 30% glycerin/water (1:1) dispersion of 30 to 60 Pa.s (20° C.) and which is used in a quantity of 10 to 20% by weight, based on the toothpaste. In addition, particularly suitable precipitated silicas of this type have rounded corners and edges and are commercially obtainable under the name of Sident® 12 DS (DEGUSSA).

Other precipitated silicas of this type are Sident 8 (DEGUSSA) and Sorbosil AC 39 (Crosfield Chemicals). These silicas are distinguished by a weaker thickening effect and a slightly larger mean particle size of 8 to 14 $\mu m$ for a specific BET surface of 40 to 75 $m^2/g$ and are particularly suitable for liquid tooth creams. These should have a viscosity (25° C., shear rate D =10 $s^{-1}$) of 10 to 100 Pa.s.

By contrast, toothpastes which have a far higher viscosity of more than 100 Pa.s (25° C., D=10 $s^{-1}$) require a sufficiently high percentage content of silicas with a particle size of less than 5 $\mu m$, preferably at least 3% by weight of a silica with a particle size of 1 to 3 $\mu m$. Accordingly, besides the precipitated silicas mentioned, even finer so-called thickening silicas with a BET surface of 150 to 250 $m^2/g$, for example the commercial products Sipernat 22 LS or Sipernat 320 DS, are preferably added to such toothpastes.

Another polishing component which may be present in a quantity of about 1 to 5% by weight is, for example, aluminium oxide in the form of lightly calcined alumina containing γ- and α-aluminium oxide. A suitable aluminium oxide such as this is commercially obtainable under the name of "Poliertonerde P10 feinst" (Giulini Chemie).

The dental care preparations according to the invention may contain sodium fluoride, zinc fluoride, tin(II) fluoride, amine fluoride or sodium monofluorophosphate, for example, as fluorine compounds. A quantity of 0.01 to 0.2% by weight fluorine in the form of the compounds mentioned should preferably be present.

Glycerin, sorbitol, xylitol, propylene glycol, polyethylene glycol or mixtures thereof may be used as humectants. The dental care preparations according to the invention preferably contain a mixture of glycerin, sorbitol and polyethylene glycol in a ratio by weight of 10:(8–12):(0.1–1) as humectant.

Suitable binders and consistency factors are, for example, natural and synthetic water-soluble polymers such as, for example, carrageen, tragacanth, guar, cellulose and nonionic derivatives thereof such as, for example, hydroxyethyl cellulose or methyl hydroxypropyl cellulose. Agar agar, xanthan gum, pectins, water-soluble carboxyvinyl polymers (for example Carbopol® types), polyvinyl alcohol, polyvinyl pyrrolidone and relatively high molecular weight polyethylene glycols (with molecular weights of $10^3$ to $10^6$ D) are also suitable as binders and thickeners.

Suitable non-cationic bactericidal components are, for example, phenols, resorcinols, bisphenols, salicylanilides and halogenated derivatives thereof, halogenated carbanilides and p-hydroxybenzoic acid esters. Particularly preferred antimicrobial components are halogenated diphenylethers, for example 2,4-dichloro-2'hydroxydiphenyl ether, 4,4'-dichloro-2'-hydroxydiphenyl ether, 2,4,4'-tribromo-2'-hydroxydiphenyl ether and 2,4,4'-trichloro-2'-hydroxydiphenyl ether (Triclosan). They are preferably used in quantities of 0.01 to 1% by weight in the dental care preparations according to the invention. In one particularly preferred embodiment, Triclosan is used in a quantity of 0.01 to 0.3% by weight.

D-panthenol [D- (+)- 2,4-dihydroxy-N-(3-hydroxypropyl)-3,3-di-methylbutyramide] corresponds in its biological activity to pantothenic acid. Pantothenic acid (R–(+)– N–(2,4-dihydroxy-3,3-dimethylbutyryl-β-alanine) is an intermediate stage in the biosynthesis of the coenzyme A and is classed as a vitamin B complex ($B_3$). These substances are known to promote the healing of wounds and to have a favorable effect on the skin. Accordingly, they have also occasionally been described in connection with toothpastes. The dental care preparations according to the invention preferably contain 0.05 to 5% by weight of panthenol or a salt of pantothenic acid.

Retinol (3,7-dimethyl-9-(2,6,6-trimethyl-1-cyclohexenyl)-2,4,6,4-nonatetraen-1-ol is the international generic name for vitamin $A_1$. Instead of retinol itself, one of its derivatives with similar biological activity, for example an ester or retinoic acid (tretinoin), one of its salts or its esters may also be used. A retinol ester, more particularly a fatty acid ester of a $C_{12-22}$ fatty acid, is preferably used. Retinol palmitate is particularly suitable. Where a retinol ester, for example retinol palmitate with an activity of $1.7·10^6$ I.U. per g is selected, it is preferably used in a quantity of 0.001 to 0.1% by weight. Where other retinol derivatives are used, a quantity corresponding to a concentration of $10^3$ to $10^6$ I.U. (International Units) per 100 g is recommended.

Besides polishing components, fluorine compounds, humectants and binders, preferred dental care preparations according to the invention preferably contain 0.01 to 1% by weight of a halogenated diphenyl ether,
0.05 to 5% by weight of panthenol or a salt of pantothenic acid and
0.01 to 0.1% by weight of a retinol ester, preferably retinol palmitate.

Besides the compulsory components mentioned, the dental care preparations according to the invention may contain other auxiliaries and additives known per se. An additive which has long been known as a toothpaste component is particularly effective in the dental care preparations according to the invention, namely: calcium glycerophosphate, the calcium salt of glycerol-1-phosphoric acid or glycerol-2-phosphoric acid or glycerol-3-phosphoric acid, the mirror-image isomer of glycerol-1-phosphoric acid, or a mixture of these acids. This compound has a remineralizing effect in toothpastes because it yields both calcium and phosphate ions. Calcium glycerophosphate is preferably used in quantities of 0.01 to 1% by weight in the dental care preparations according to the invention. Overall, the dental care preparations according to the invention may contain typical auxiliaries and additives in quantities of up to 10% by weight.

The organoleptic qualities of the dental care preparations according to the invention may be improved, for example, by addition of flavoring oils and sweeteners.

Suitable flavoring oils are any of the natural and synthetic flavors typically used for oral and dental care preparations. Natural flavors may be present both in the form of the natural essential oils isolated from drugs and in the form of the individual components isolated therefrom.

Suitable flavoring agents are, for example, peppermint oil, spearmint oil, eucalyptus oil, aniseed oil, fennel oil, caraway oil, menthyl acetate, cinnamaldehyde, anethol, vanillin, thymol and mixtures of these components.

Suitable sweetening agents are, for example, saccharin sodium, sodium cyclamate, sucrose, lactose, maltose, fructose.

Other typical auxiliaries and additives for toothpastes are:

surfactants, preferably anionic, zwitterionic, amphoteric, nonionic surfactants or a combination of several different surfactants solvents and solubilizers, for example lower monohydric or polyhydric alcohols or ethers, for example ethanol, 1,2-propylene glycol, diethylene glycol or butyl diglycol pigments, for example titanium dioxide dyes buffers, for example primary, secondary or tertiary alkali metal phosphates or citric acid/Na citrate other wound-healing or anti-inflammatory agents, for example allantoin, urea, azulene, camomile-based active principles, acetylsalicylic acid derivatives or thiocyanate other vitamins such as, for example, ascorbic acid, biotin, tocopherol or rutin mineral salts such as, for example, manganese, zinc or magnesium salts.

The following Examples are intended to illustrate the invention.

EXAMPLES

I. Toothpastes According to the Invention were Prepared from the Following Ingredients:

|  | 1 | 2 |
|---|---|---|
| Water | to 100 | to 100 |
| Sorbitol | 20.0 | 20.0 |

-continued

|  | 1 | 2 |
|---|---|---|
| Glycerin | 21.0 | 21.0 |
| Polyethylene glycol 1550 | 2.0 | 1.0 |
| Sident 8 SPLS | 12.0 | — |
| Sident 12 SPLS | — | 12.0 |
| Sident 22 LS | 8.0 | 5.5 |
| Sipernat 320 DS | 1.0 | 0.5 |
| $TiO_2$ | 1.0 | 1.0 |
| $Na_2HPO_4$ | 0.20 | 0.20 |
| $Na_3PO_4$ | 0.25 | 0.25 |
| Saccharin Na | 0.20 | 0.20 |
| Na benzoate | — | 0.49 |
| Na fluoride | 0.32 | 0.32 |
| Phosphoric acid | — | 0.1 |
| Carboxymethyl cellulose | 0.6 | — |
| Xanthan gum | — | 0.8 |
| Na lauryl sulfate | 1.35 | 1.35 |
| $MgSO_4.7H_2O$ | 0.210 | 0.210 |
| $ZnSO_4.7H_2O$ | 0.088 | 0.088 |
| $MnSO_4.H_2O$ | 0.011 | 0.011 |
| Dyes | 0.55 | 0.0055 |
| Ca glycerophosphate | 0.130 | 0.130 |
| Triclosan | 0.100 | 0.100 |
| Vitamin $A_1$ palmitate (1.7 million I.U./g) | 0.018 | 0.03 |
| D-panthenol (50%) | 0.50 | 0.25 |
| Flavoring 1.00 | 1.00 | |

II. Liquid Tooth Creams According to the Invention

|  | 3 | 4 | 5 |
|---|---|---|---|
| Water | to 100 | to 100 | to 100 |
| Sorbitol (70%) | 30.0 | 30.0 | 30.0 |
| Glycerin (86%) | 33.0 | 33.0 | 33.0 |
| Polyethylene glycol 1550 | 1.0 | 1.0 | 1.0 |
| Ethanol (93.8%) | 2.0 | 2.0 | 2.0 |
| Sident 8 | 12.0 | 12.0 | — |
| Sident 12 SPLS | — | — | 12.0 |
| $TiO_2$ | 1.0 | 1.0 | — |
| $Na_2HPO_4$ | 0.2 | 0.2 | 0.2 |
| Saccharin Na | 0.2 | 0.2 | 0.2 |
| Na benzoate | 0.49 | 0.49 | 0.5 |
| Na fluoride | 0.32 | 0.23 | 0.33 |
| Xanthan gum | 0.5 | 0.5 | 0.3 |
| Na lauryl sulfate | 1.5 | 1.5 | 1.5 |
| PEG 30 glyceryl stearate | 0.5 | 0.5 | 0.5 |
| $MgSO_4.7 H_2O$ | 0.21 | 0.21 | 0.21 |
| $ZnSO_4.7 H_2O$ | 0.088 | 0.088 | 0.088 |
| $MnSO_4.H_2O$ | 0.011 | 0.011 | 0.011 |
| Dyes | 0.0055 | 0.0055 | 0.00067 |
| Ca glycerophosphate | 0.13 | 0.13 | — |
| Triclosan | 0.1 | 0.1 | 0.3 |
| Vitamin A palmitate (1.7 million I.U./g) | 0.018 | 0.01 | 0.025 |
| D-panthenol (50%) | 0.5 | 0.5 | 0.26 |
| Flavoring | 1.0 | 1.0 | 1.0 |

III. Clinical Comparison

The liquid tooth cream of Example 3 (A) was compared with a corresponding placebo tooth cream (B) which contained water instead of the components vitamin A palmitate and panthenol.

Two groups of forty volunteers left their teeth completely uncleaned for three days in order to develop gingivitis in accordance with the experimental gingivitis test.

Thereafter one group used toothpaste (A) (invention) and the other group toothpaste (B) in the usual way for 1 minute twice a day. On the first day of application of the tooth cream and on the 7th day, the following parameters were determined on 12 teeth by qualified dentists using mirror and probe:

Silness-Löe gingival index (score 0–3 points)
degree of inflammation (score 0–3 points)
spontaneous pain sensation (score 0–3 points).

In addition, the volunteers completed a questionnaire in order to determine the acceptance of the products.

Results

The scores are shown as the average points score of all volunteers (n=number of volunteers). The standard deviation is shown in brackets.

1. Gingivitis Index

|  | n | Tooth cream A (Example 3) | n | Placebo cream (B) |
|---|---|---|---|---|
| 1st Day | 40 | 1.252 (0.519) | 40 | 1.199 (0.473) |
| 7th Day | 40 | 0.116* (0.149) | 40 | 0.499* (0.385) |

*The statistical significance (Kruskal-Wallis Test) is 99.9%.

The calculated gingivitis reduction is thus
1.136 (points) for the tooth cream according to the invention as against only
0.7 (points) for the placebo tooth cream without vitamin A palmitate and panthenol.

2. Degree of Inflammation

|  | n | Tooth cream A (Example 3) | n | Placebo cream (B) |
|---|---|---|---|---|
| 1st Day | 40 | 1.325 | 40 | 1.3 |
| 7th Day | 40 | 0.30* | 40 | 0.525* |

*Statistical significance: 95%

3. Spontaneous Pain Sensation

|  | n | Tooth cream A (Example 3) | n | Placebo cream (B) |
|---|---|---|---|---|
| 1st Day | 40 | 0.65 | 40 | 0.57 |
| 7th Day | 40 | 0.0 | 40 | 0.07 |

The results of the clinical comparison clearly show that tooth cream (A) according to the invention (Example 3) reduces gingivitis and inflammation more distinctly than the placebo cream within the first week of application.

What is claimed is:

1. A dental care composition comprising:
   (a) at least one panthenol compound that is panthenol or a salt of pantothenic acid;
   (b) at least one retinol compound that is retinol or a derivative thereof;
   (c) at least one antibacterial compound, wherein the antibacterial compound comprises at least one halogenated diphenyl ether; and
   (d) from 5 weight percent to 50 weight percent, based on the total weight of the composition, of at least one polishing component wherein the composition comprises less than 5 weight percent of calcium containing polishing components selected from the group consisting of chalk, calcium pyrophosphate and dicalcium phosphate.

2. The dental care composition of claim 1 further comprising one or more humectants, fluorine compounds or binders, or combinations thereof.

3. The dental care composition of claim 2 wherein the antibacterial compound further comprises at least one compound that is a phenol, resorcinol, bisphenol or salicylanilide, a halogenated derivative of a phenol, resorcinol, bisphenol or salicylanilide, a halogenated carbanilide, or a p-hydroxybenzoic acid ester, or combinations thereof.

4. The dental care composition of claim 1 wherein the dental care composition comprises from 0.01 weight percent to 1 weight percent of the halogenated diphenyl ether, and from 0.05 weight percent to 5 weight percent of the panthenol compound, wherein the percentages are based on the total weight of the composition.

5. The dental care composition of claim 4 wherein the retinol compound is a retinol ester.

6. The dental care composition of claim 5 wherein the retinol ester is present in an amount ranging from 0.001 weight percent to 0.1 weight percent based on the total weight of the composition.

7. The dental care composition of claim 6 wherein the halogenated diphenyl ether is 2,4-dichloro-2'-hydroxydiphenyl ether, 4,4'-dichloro-2'-hydroxydiphenyl ether, 2,4,4'-tribromo-2'-hydroxydiphenyl ether or 2,4,4'-trichloro-2'-hydroxydiphenyl ether, or combinations thereof.

8. The dental care composition of claim 2 further comprising one or more auxiliary compounds in an amount of up to 10 weight percent based on the total weight of the composition.

9. The dental care composition of claim 8 wherein at least one of the auxiliary compounds is calcium glycerophosphate in an amount of from 0.01 weight percent to 1 weight percent based on the total weight of the composition.

10. The dental care composition of claim 1 wherein the composition comprises less than 5 weight percent of calcium containing polishing components.

11. The dental care composition of claim 1 wherein the dental care composition reduces inflammation of gums.

12. A dental care composition comprising:
   (a) at least one panthenol compound that is panthenol or a salt of pantothenic acid;
   (b) at least one retinol compound that is retinol or a derivative thereof;
   (c) at least one non-cationic bactericidal compound that is a halogenated diphenyl ether;
   (d) one or more dental care compounds selected from the group consisting of polishing components, humectants, fluorine compounds, binders and combinations thereof.

13. A dental care composition comprising:
   (a) from 0.01 weight percent to 1 weight percent of at least one halogenated diphenyl ether;
   (b) from 0.05 weight percent to 5 weight percent of at least one panthenol compound that is panthenol or a salt of pantothenic acid;
   (c) from 0.01 weight percent to 0.1 weight percent of a retinol ester; and
   (d) from 5 weight percent to 50 weight percent, based on the total weight of the composition, of at least one polishing component wherein the composition comprises less than 5 weight percent of calcium containing polishing components selected from the group consisting of chalk, calcium pyrophosphate and dicalcium phosphate.

14. The dental care composition of claim 13 further comprising one or more humectants, fluorine compounds or binders, or combinations thereof.

15. The dental care composition of claim 14 wherein the retinol ester is retinol palmitate.

16. A method of reducing inflammation of gums comprising:
   (a) forming a dental care composition comprising
      (i) at least one panthenol compound that is panthenol or a salt of pantothenic acid;
      (ii) at least one retinol compound that is retinol or a derivative thereof;
      (iii) at least one antibacterial compound, wherein the antibacterial compound comprises at least one halogenated diphenyl ether; and
      (iv) from 5 weight percent to 50 weight percent, based on the total weight of the composition, of at least one polishing component wherein the composition comprises less than 5 weight percent of calcium containing polishing components selected from the group consisting of chalk, calcium pyrophosphate and dicalcium phosphate; and
   (b) contacting the dental care composition with teeth or gums, or combinations thereof.

* * * * *

UNITED STATES PATENT AND TRADEMARK OFFICE
CERTIFICATE OF CORRECTION

PATENT NO.    : 6,491,899 B1
DATED         : December 10, 2002
INVENTOR(S)   : Leinen et al.

It is certified that error appears in the above-identified patent and that said Letters Patent is hereby corrected as shown below:

Column 1,
Line 4, insert the following on consecutive lines:

-- CROSS REFERENCE TO RELATED APPLICATIONS

This application is a national stage application under 35 U.S.C. §371 of international application PCT/EP99/05210 filed on July 21, 1999, the international application not being published in English. --

Signed and Sealed this

Twelfth Day of August, 2003

JAMES E. ROGAN
*Director of the United States Patent and Trademark Office*